(12) United States Patent
Adler

(10) Patent No.: US 6,872,942 B1
(45) Date of Patent: Mar. 29, 2005

(54) HIGH-SPEED INSPECTION OF FLAT SUBSTRATES WITH UNDERLYING VISIBLE TOPOLOGY

(75) Inventor: David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/701,857

(22) Filed: Nov. 5, 2003

Related U.S. Application Data

(60) Provisional application No. 60/459,432, filed on Apr. 1, 2003.

(51) Int. Cl.[7] .......................... G01N 23/22; G21K 3/10; H01J 37/20
(52) U.S. Cl. ....................... 250/306; 250/307; 250/310; 250/397; 250/398; 250/400; 250/491.1; 250/492.3
(58) Field of Search ................................. 250/306, 307, 250/310, 397, 398, 400, 491.1, 492.3

(56) References Cited

U.S. PATENT DOCUMENTS

| | | | | |
|---|---|---|---|---|
| 6,465,781 B1 | * | 10/2002 | Nishimura et al. | ......... 250/306 |
| 6,566,897 B2 | * | 5/2003 | Lo et al. | ..................... 324/751 |
| 6,618,134 B2 | * | 9/2003 | Vaez-Iravani et al. | ... 356/237.4 |
| 6,636,302 B2 | | 10/2003 | Nikoonahad et al. | |
| 6,673,637 B2 | | 1/2004 | Wack et al. | |

* cited by examiner

*Primary Examiner*—Nikita Wells
(74) *Attorney, Agent, or Firm*—Okamoto & Benedicto LLP

(57) ABSTRACT

One embodiment disclosed relates to a method for inspecting a substrate. The method includes exposing the substrate to an incident beam, inducing relative motion between the incident beam and the substrate, and detecting charged particles emitted from the substrate. The relative motion is such that the beam travels over a surface of the substrate along a substantially spiral shaped path.

14 Claims, 5 Drawing Sheets

HIGH-SPEED INSPECTION OF FLAT SUBSTRATES WITH UNDERLYING VISIBLE TOPOLOGY

CROSS-REFERENCE TO RELATED APPLICATIONS

The present application claims the benefit of provisional patent application No. 60/459,432, filed Apr. 1, 2003, entitled "High-Speed Inspection Of Flat Substrates With Underlying Visible Topology", by inventor David L. Adler, the disclosure of which is herby incorporated by reference.

BACKGROUND OF THE INVENTION

1. Field of the Invention

The present invention relates generally to automated substrate inspection methods and apparatus.

2. Description of the Background Art

Prior techniques for inspection of substantially smooth or flat substrates include inspection with optical tools. However, optical tools may be confused by underlying topology, if such underlying topology is visible to the optical inspector. In particular, false defects may be found in the smooth surface due to features in the underlying visible topology. Regarding conventional electron beam inspection tools, they are slow and ineffective in such inspections of smooth substrates.

The above-described problems and disadvantages may be overcome by utilizing embodiments of the present invention.

SUMMARY

One embodiment of the invention pertains to a first method for inspecting a substrate. The method includes exposing the substrate to an incident beam, inducing relative motion between the incident beam and the substrate, and detecting charged particles emitted from the substrate. The relative motion is such that the beam travels over a surface of the substrate along a substantially spiral shaped path.

Another embodiment of the invention relates to a second method for inspecting a substrate. This method includes exposing the substrate to an incident beam of charged particles using a column. Said beam causes charged particles to be emitted from the substrate. The emitted charged particles are detected using multiple detector elements, where the multiple detector elements are positioned outside the column.

Another embodiment of the invention relates to a third method for inspection a substrate. The method includes exposing the substantially flat substrate with an incident beam of charged particles using a column, where said incident beam causing charged particles to be emitted from the substrate. The emitted charged particles are detected using multiple detector elements. A signal derived from the multiple detector elements is processed to be relatively sensitive to topological contrast and relatively insensitive to material contrast.

Another embodiment of the invention relates to a first apparatus for inspecting a substrate. The apparatus includes a column for exposing the substrate to an incident beam, and a spiral motion mechanism for inducing relative motion between the incident beam and the substrate such that the beam travels over a surface of the substrate along a substantially spiral shaped path. At least one detector is used for detecting charged particles emitted from the substrate.

Another embodiment of the invention relates to a second apparatus for inspecting a substrate. The apparatus includes a column for exposing the substrate to an incident beam of charged particles, said beam causing charged particles to be emitted from the substrate, and multiple detector elements for detecting the emitted charged particles. In accordance with this embodiment, the multiple detector elements are positioned outside the column.

Another embodiment of the invention relates to a third apparatus for inspecting a substrate. The apparatus includes a column for exposing the substrate with an incident beam of charged particles, said incident beam causing charged particles to be emitted from the substrate, and multiple detector elements are used for detecting the emitted charged particles. Here, the apparatus further includes a signal processor adapted to process a signal derived from the multiple detector elements to be relatively sensitive to topological contrast and relatively insensitive to material contrast.

DETAILED DESCRIPTION

Figure 1:
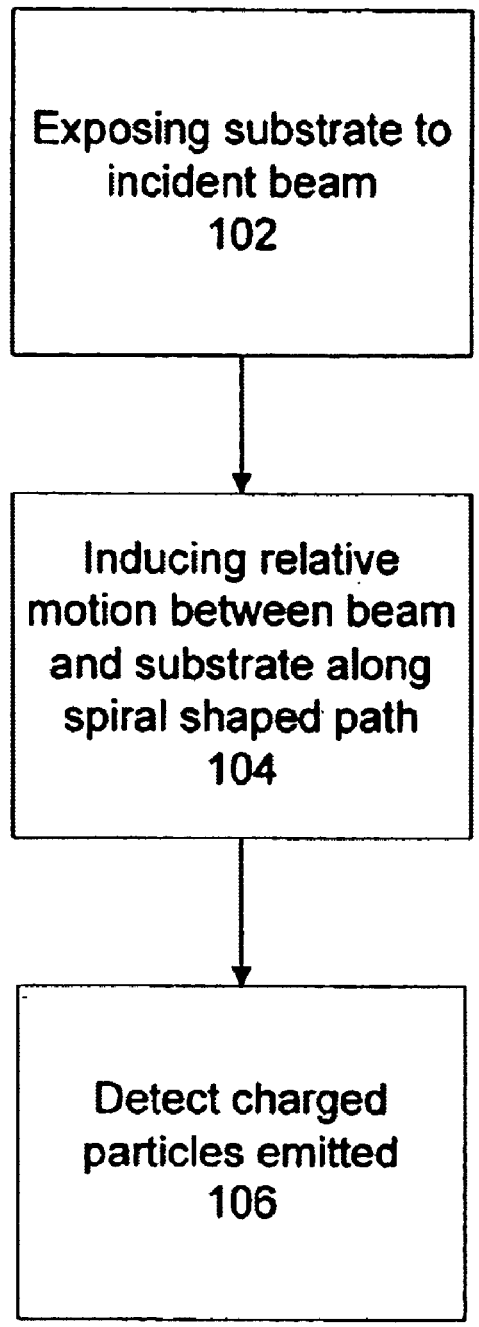
FIG. 1 is a flow chart depicting a first method for inspection of a substrate in accordance with an embodiment of the invention.

FIG. 1 is a flow chart depicting a first method for inspection of a substrate in accordance with an embodiment of the invention. The method as depicted Includes at least three steps.

In a first step 102, the substrate is exposed to an incident beam. For example, the incident beam may comprise an electron beam from a column. The incident beam may be within a vacuum. For example, the vacuum system could be implemented as a Whistler type device. Advantageously, the incident beam is such that the incident electrons (or other charged particles) does not penetrate much past the surface, so the inspector will not receive confusing signals due to the underlying topology.

Figure 4:
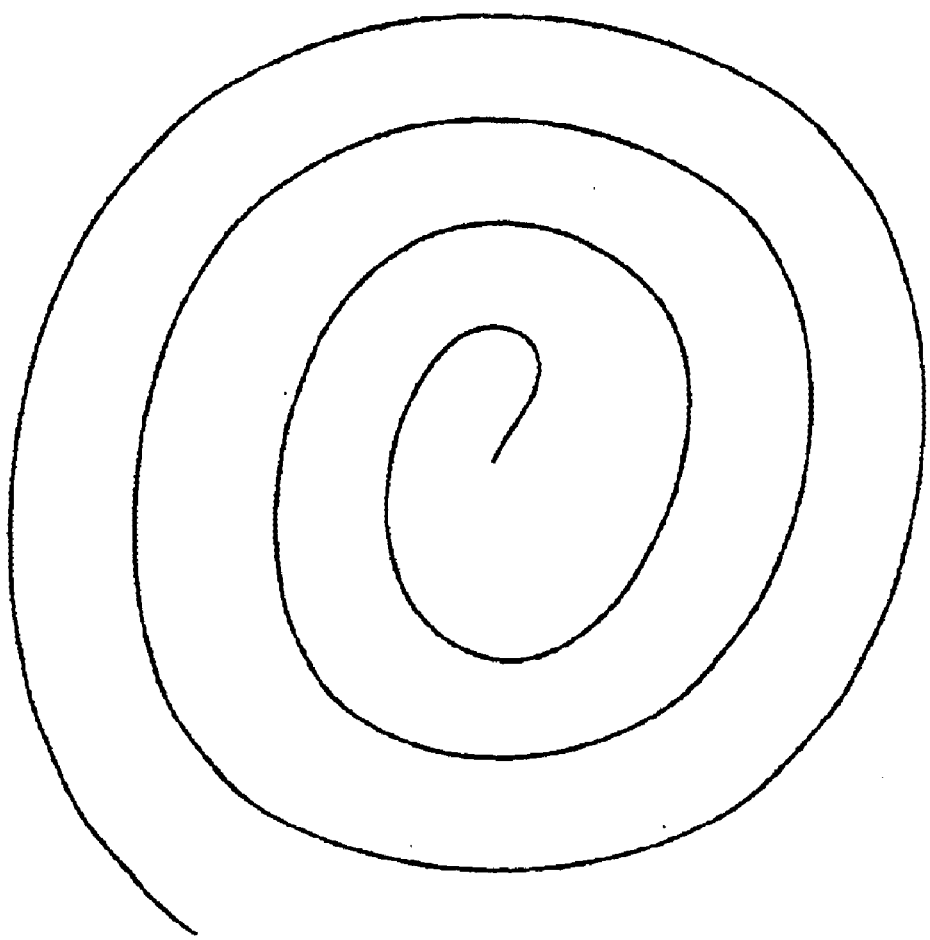
FIG. 4 illustrates a spiral shaped path for the relative motion between the incident beam and the substrate in accordance with an embodiment of the invention.

In a second step 104, relative motion is induced between the incident beam and the substrate. The relative motion is advantageously along a substantially spiral shaped path. An illustration of an example of such a spiral shaped path is depicted in FIG. 4. For example, the spiral relative motion may be caused, at least in part, by motor elements located preferably outside a vacuum chamber. Such spiral relative motion involves simultaneous rotation and translation. Either the rotational or translational movements by a motor may be replaced or augmented by deflecting the incident beam. The relative motion in both rotational and translational dimensions is believed by the applicant to advantageously facilitate detection of defects on the smooth surface.

In a third step 106, charged particles emitted from the substrate are detected. The charged particles may be, for example, electrons emitted from the substrate due to the impingement of the incident beam. In one embodiment, an energy filter may be used to filter the emitted charged particles such that those emitted charged particles that are detected preferentially or essentially consist of backscattered electrons.

In one embodiment, charge at a surface of the substrate may be controlled by illuminating the surface with electrons having a low landing energy. These low landing energy electrons may compensate for electrons emitted from the surface. In one implementation, the low landing energy electrons may be provided concurrently with the incident beam so as to concurrently compensate for emitted electrons. In another implementation, the low landing energy electrons may be provided in an alternating fashion relative to the incident beam so as to periodically compensate for charge build-up at the surface.

Figure 2:
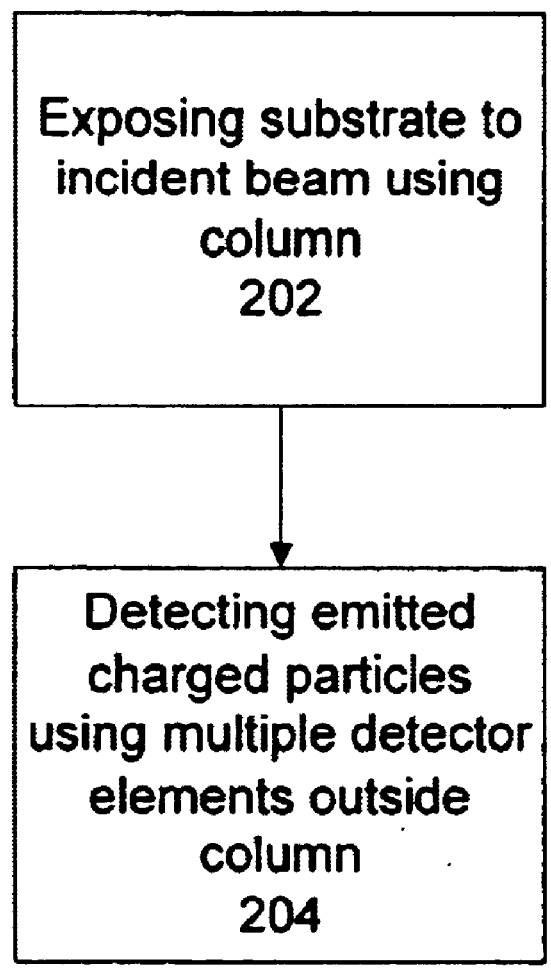
FIG. 2 is a flow chart depicting a second method for inspection of a substrate in accordance with an embodiment of the invention.

FIG. 2 is a flow chart depicting a second method for inspection of a substrate in accordance with an embodiment of the invention. The method as depicted includes at least two steps.

In a first step 202, the substrate is exposed to an incident beam of charged particles using a column. The incident beam may be within a vacuum. The charged particles from the incident beam causing charged particles to be emitted from the substrate. For example, the incident beam may comprise incident electrons, and the emitted charged particles may comprise scattered electrons caused by the incident electrons. Advantageously, the incident beam is such that the incident electrons (or other charged particles) does not penetrate much past the surface, so the inspector will not receive confusing signals due to the underlying topology.

Figure 5:
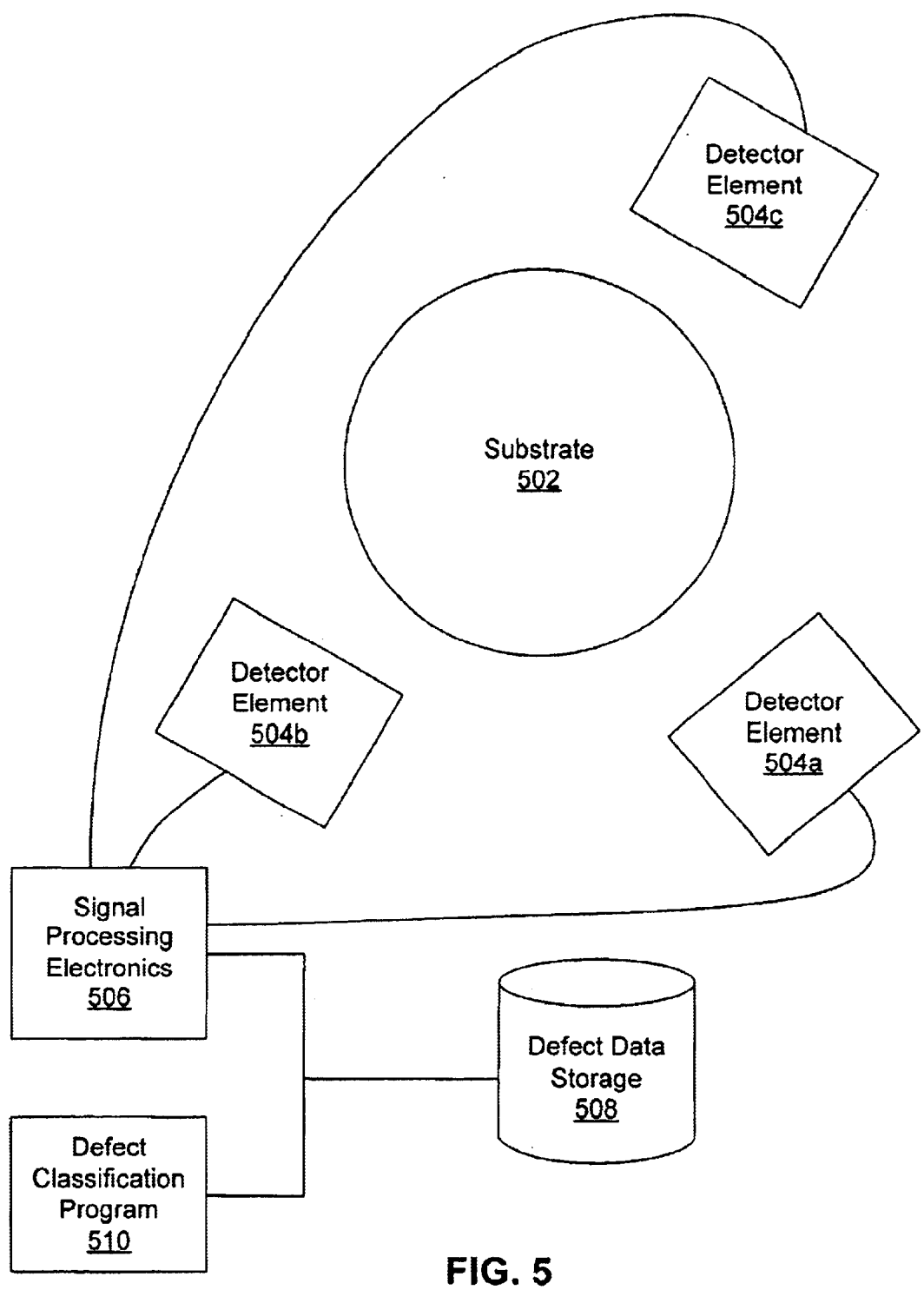
FIG. 5 illustrates an example configuration including multiple detector elements around a periphery of a substrate in accordance with an embodiment of the invention.

In a second step 204, charged particles emitted from the substrate are detected using multiple detector elements. Here, the multiple detector elements are positioned outside the column. In one implementation, at least some of the detectors may be positioned around a periphery of the substrate. The use of such multiple detector elements advantageously provides for multiple detection signals that may be used for differential detection. The differential detection may be used to effectively find defects. For example, signal from material contrast or charging may be eliminated, and topological difference may be highlighted, by use of such differential detection. An illustration of an example configuration of detector elements 504 around a periphery of a substrate 502 is depicted in FIG. 5. While three detector elements are illustrated in FIG. 5, in general two or more detector elements may be used to achieve the differential detection.

In one embodiment, charge at a surface of the substrate may be controlled by illuminating the surface with electrons having a low landing energy. These low landing energy electrons may compensate for electrons emitted from the surface. In one implementation, the low landing energy electrons may be provided concurrently with the incident beam so as to concurrently compensate for emitted electrons. In another implementation, the low landing energy electrons may be provided in an alternating fashion relative to the incident beam so as to periodically compensate for charge build-up at the surface.

Figure 3:
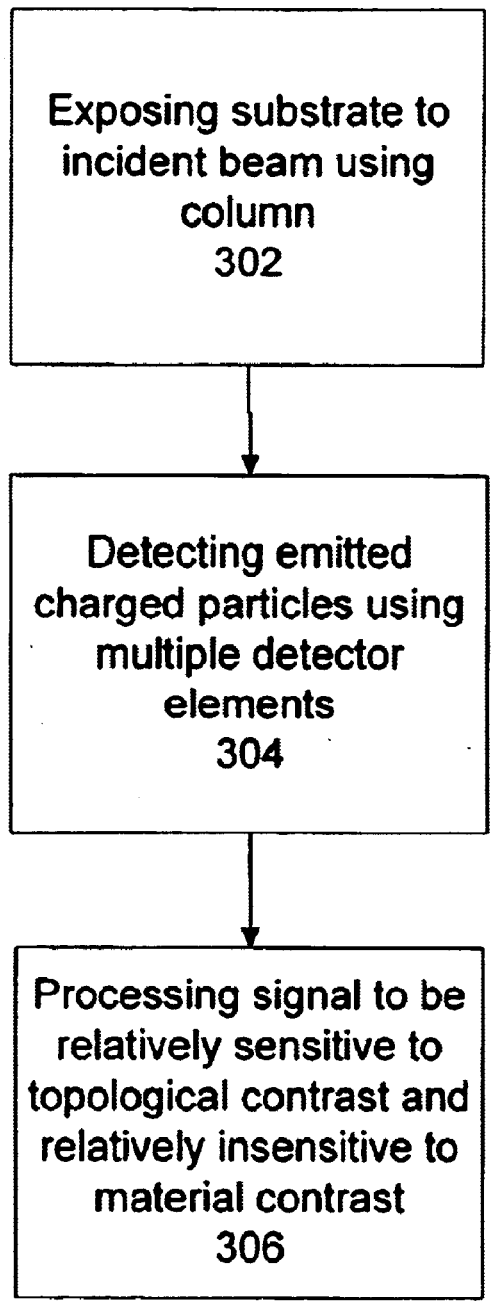
FIG. 3 is a flow chart depicting a third method for inspection of a substrate in accordance with an embodiment of the invention.

FIG. 3 is a flow chart depicting a third method for inspection of a substrate in accordance with an embodiment of the invention. The method as depicted includes at least three steps.

In a first step 302, the substrate is exposed to an incident beam. For example, the incident beam may comprise an electron beam from a column. The incident beam may be within a vacuum. Advantageously, the incident beam is such that the incident electrons (or other charged particles) does not penetrate much past the surface, so the inspector will not receive confusing signals due to the underlying topology.

In a second step 304, charged particles emitted from the substrate are detected using multiple detector elements. Here, the multiple detector elements may be positioned outside the column; for example, at least some of the detectors may be positioned around a periphery of the substrate. The use of such multiple detector elements advantageously provides for multiple detection signals that may be used for differential detection. The differential detection may be used to effectively find defects. For example, signal from material contrast or charging may be eliminated, and topological difference may be highlighted, by use of such differential detection. An illustration of an example configuration of detector elements 504 around a periphery of a substrate 502 is depicted in FIG. 5. While three detector elements are illustrated in FIG. 5, in general two or more detector elements may be used to achieve the differential detection.

In a third step 306, a signal derived from the multiple detector elements is processed to create a differential detection signal. The processing is such that the differential detection signal becomes relatively sensitive to topological contrast and relatively insensitive to material contrast. In one embodiment, the signal may also be processed to distinguish between pits and particles present on the surface.

Such processing may be done using signal processing electronics and/or software 506 that is coupled to receive signals from the multiple detection elements 504. See, for example, FIG. 5 for an illustration. In addition, defect locations may be saved in defect data storage 508, or a review mode may be included in the tool. In one embodiment, a classification program 510 may be used to determine a general shape or other classification of defects. For example, the defects may be classified as to whether they result from pits, from scratches, or from particles.

Optionally, optical inspection may be combined into the apparatus. For example, using a common stage, a common handler, and so on.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for inspecting a substrate, the method comprising:

exposing the substrate to an incident beam;

inducing relative motion between the incident beam and the substrate such that the beam travels over a surface of the substrate along a substantially spiral shaped path; and detecting charged particles emitted from the substrate.

2. The method of claim 1, wherein the relative motion is caused, at least in part, by motor elements located outside a vacuum chamber.

3. The method of claim 1 further comprising:

controlling charge at a surface of the substrate by illuminating the surface with electrons having a low landing energy.

4. The method of claim 3, wherein the low landing-energy electrons are provided concurrently with the incident beam.

5. The method of claim 3, wherein the low landing-energy electrons are provided in an alternating fashion relative to the incident beam.

6. A method for inspecting a substrate, the method comprising:

exposing the substrate to an incident beam of charged particles using a column, said beam causing charged particles to be emitted from the substrate; a spiral motion mechanism for inducing relative motion between the incident beam and the substrate such that the beam travels over a surface of the substrate along a substantially spiral shaped path, and detecting the emitted charged particles using multiple detector elements, wherein the multiple detector elements are positioned outside the column.

7. The method of claim 6 further comprising:

filtering the emitted charged particles such that those emitted charged particles that are detected consist essentially of backscattered electrons.

8. The method of claim 6, wherein at least some of the detectors are positioned around a periphery of the substrate.

9. The method of claim 6 further comprising:

controlling charge at a surface of the substrate by illuminating the surface with electrons having a low landing energy.

10. A method for inspecting a substantially flat substrate, the method comprising:

exposing the substrate with an incident beam of charged particles using a column, said incident beam causing charged particles to be emitted from the substrate; a spiral motion mechanism for inducing relative motion between the incident beam and the substrate such that the beam travels over a surface of the substrate along a substantially spiral shaped path; and detecting the emitted charged particles using multiple detector elements; and processing a signal derived from the multiple detector elements to be relatively sensitive to topological contrast and relatively insensitive to material contrast.

11. The method of claim 10, wherein the signal is processed to distinguish between pits and particles present on the surface.

12. An apparatus for inspecting a substrate, the apparatus comprising:

a column for exposing the substrate to an incident beam;

a spiral motion mechanism for inducing relative motion between the incident beam and the substrate such that the beam travels over a surface of the substrate along a substantially spiral shaped path; and at least one detector for detecting charged particles emitted from the substrate.

13. An apparatus for inspecting a substrate, the apparatus comprising:

a column for exposing the substrate to an incident beam of charged particles, said beam causing charged particles to be emitted from the substrate; a spiral motion mechanism for inducing relative motion between the incident beam and the substrate such that the beam travels over a surface of the substrate along a substantially spiral shaped path; and multiple detector elements for detecting the emitted charged particles, wherein the multiple detector elements are positioned outside the column.

14. An apparatus for Inspecting a substrate, the apparatus comprising:

a column for exposing the substrate with an incident beam of charged particles, said incident beam causing charged particles to be emitted from the substrate; a spiral motion mechanism for inducing relative motion between the incident beam and the substrate such that the beam travels over a surface of the substrate along a substantially spiral shaped path; and multiple detector elements for detecting the emitted charged particles; and a signal processor adapted to process a signal derived from the multiple detector elements to be relatively sensitive to topological contrast and relatively insensitive to material contrast.

* * * * *